United States Patent [19]

Takeuchi et al.

[11] Patent Number: 4,510,036

[45] Date of Patent: Apr. 9, 1985

[54] LIMITING ELECTRIC CURRENT TYPE OXYGEN SENSOR WITH HEATER AND LIMITING ELECTRIC CURRENT TYPE OXYGEN CONCENTRATION DETECTING DEVICE USING THE SAME

[75] Inventors: Takashi Takeuchi; Hideaki Takahashi; Keiichi Saji; Haruyoshi Kondo; Kiyoharu Hayakawa, all of Aichi, Japan

[73] Assignee: Kabushiki Kaisha Toyota Chuo Kenkyusho, Aichi, Japan

[21] Appl. No.: 457,888

[22] Filed: Jan. 14, 1983

[30] Foreign Application Priority Data

Jan. 21, 1982 [JP] Japan ................................. 57-6846

[51] Int. Cl.³ ............................................ G01N 27/58
[52] U.S. Cl. .................................... 204/425; 204/426; 204/408
[58] Field of Search ............... 204/406, 408, 424, 425, 204/426

[56] References Cited

U.S. PATENT DOCUMENTS

| | | | |
|---|---|---|---|
| 3,767,469 | 10/1973 | Flais et al. | 204/424 X |
| 3,948,081 | 4/1976 | Wessel et al. | 204/408 X |
| 4,107,019 | 8/1978 | Takao et al. | 204/426 X |
| 4,129,099 | 12/1978 | Howarth | 204/427 X |
| 4,212,720 | 7/1980 | Maurer et al. | 204/424 |
| 4,300,990 | 11/1981 | Maurer | 204/425 X |
| 4,304,652 | 12/1981 | Chiba et al. | 204/426 X |
| 4,334,974 | 6/1982 | Muller et al. | 204/425 |
| 4,345,985 | 8/1982 | Tohda et al. | 204/426 X |
| 4,365,604 | 12/1982 | Sone | 204/424 X |
| 4,384,934 | 5/1983 | de Bruin et al. | 204/406 |

Primary Examiner—G. L. Kaplan
Assistant Examiner—Nam X. Nguyen

[57] ABSTRACT

The invention provides a limiting electric current type oxygen sensor with a microheater, having: an oxygen ionic conductor; an anode and a cathode respectively formed on two major surfaces of the oxygen ionic conductor; an insulating film which has a porosity of not less than 0.2 [%], an average pore diameter of not less than 140 [Å], and a thickness between 0.2 [μm] and 10 [μm], and which is formed on one of the anode and the cathode so as to regulate a flow rate of oxygen gas and to provide electrical insulation; and the microheater formed on the insulating film. The oxygen ionic conductor is electrically insulated from the microheater through the insulating film. The invention also provides a limiting electric current type oxygen concentration detecting device having the limiting electric current type oxygen sensor and a constant temperature control circuit.

8 Claims, 48 Drawing Figures

OXYGEN IONIC CONDUCTOR SUBSTRATE
$ZrO_2 + 8[mol\%] Y_2O_3$ $2 \times 2 \times 0.2$ [mm]

Pt ELECTRODE

THIN $Al_2O_3$ FILM

Pt HEATER PATTERN

OXYGEN IONIC CONDUCTOR SUBSTRATE ($ZrO_2 + 8$ [mol%] $Y_2O_3$)

$2 \times 2 \times 0.2$ [mm]

Pt ELECTRODE $Al_2O_3$ FILM

HOLE FOR REGULATING OXYGEN GAS FLOW RATE

50 [μm$^\phi$] Pt LEAD WIRES

LIMITING ELECTRIC CURRENT TYPE OXYGEN SENSOR WITH HEATER AND LIMITING ELECTRIC CURRENT TYPE OXYGEN CONCENTRATION DETECTING DEVICE USING THE SAME

RELATED APPLICATIONS

The following U.S. patent applications which are assigned to the same assignee as the instant application are related to the instant application and are incorporated herein by reference:

1. "Equipment for detecting oxygen concentration" by Haruyoshi Kondo, Keiichi Saji and Takashi Takeuchi, having U.S. Ser. No. 373,257 and filed on Apr. 29, 1982; and
2. "Oxygen sensor with heater" by Hideaki Takahashi, Kiyoharu Hayakawa, Haruyoshi Kondo and Takashi Takeuchi, having U.S. Ser. No. 404,900 and filed on Aug. 3, 1982.

BACKGROUND OF THE INVENTION

I. Field of the Invention

The present invention relates to equipment employable for detecting the concentration of oxygen in a gas and, more particularly, to a limiting electric current type oxygen sensor with a heater and a limiting electric current type oxygen concentration detecting device having the limiting electric current type oxygen sensor.

The oxygen concentration detecting device in accordance with the present invention can be employed to detect the oxygen concentration of gases exhausted from various types of combustion equipment such as boilers installed in thermal power stations, or internal combustion engines mounted in automobiles.

II. Description of the Prior Art

Needless to emphasize, various types of combustion equipment such as boilers installed in thermal power stations, or internal combustion engines mounted in automobiles are commercially available and contribute to modern life in a variety of applications.

These types of equipment may emit toxic gases in a considerable amount if they are not properly operated. A demand for lower fuel consumption is also strong these days.

It is effective to perform combustion in an atmosphere containing a small amount of fuel with respect to the air content (to be referred to as a "lean" mixture) so as to decrease the toxic gas content of the exhaust gas and to decrease fuel consumption. For example, it is known that the "lean" mixture is used in a Diesel engine. It is also efficient to use the "lean" mixture in a gasoline engine to satisfy the foregoing objects.

However, even in a combustion engine operated with a "lean" mixture, soot may be exhausted to contaminate the atmospheric air and misfiring may occur to exhaust the uncombusted fuel and decrease power or the like when an air-fuel ratio is improperly determined, thus destroying the objective of the combustion engine operated with a "lean" mixture and causing the problems of air pollution and low output power. Therefore, the air-fuel ratio is the most important factor to maximize the combustion efficiency. Generally, in the detection/control technique, the parameter to be controlled (the air-fuel ratio in the "lean" mixture herein) must be detected with high precision and detected at a high speed. In the field of combustion techniques, a proper sensor has not conventionally been proposed. For example, a magnetic oxygen concentration sensor has a poor responsiveness, so that it is not suitably mounted in an automobile. A density type or a thermal conduction type sensor is adversely affected by a small amount of hydrogen ($H_2$), thus degrading measuring precision. As a result, the conventional sensors have never been suitable for controlling an internal combustion engine.

In order to eliminate the conventional drawbacks, a sensor for detecting an oxygen concentration from a limiting electric current (to be referred to as a limiting electric current type oxygen sensor hereinafter) is proposed. The oxygen sensor of this type has various advantages but yet has a few problems. In a combustion apparatus such as an automobile internal combustion engine, the temperature of the exhaust gas usually changes in accordance with the operating conditions. Therefore, the limiting electric current type oxygen sensor must be operated in a wide temperature range between the low and high temperatures. When the limiting electric current type oxygen sensor is operated at a low temperature, its internal resistance is increased to limit the measurable range of oxygen concentration. Even at a high temperature where the internal resistance is not increased, a problem is still presented in which the relationship between the oxygen concentration and the limiting electric current is slightly changed. However, this problem can be solved when the oxygen sensor is kept at a constant temperature at which the oxygen sensor can be normally operated. A heater is disposed in the vicinity of the oxygen sensor and is driven by a constant voltage source to heat the oxygen sensor in accordance with the conventional method. However, the structure of the oxygen sensor then becomes bulky. Heat conduction is degraded, thus increasing power consumption. As a result, when the flow rate of the gas to be measured varies, the temperature varies accordingly.

SUMMARY OF THE INVENTION

The present invention seeks to eliminate the conventional drawbacks, and has for its object to provide a limiting electric current type oxygen sensor which is stably operated at a low exhaust gas temperature and is easy to manufacture at low cost, and has low power consumption, short response time and simple construction.

It is another object of the present invention to provide a limiting electric current type oxygen concentration detecting device which uses the limiting electric current type oxygen sensor so as to keep the sensor at a constant temperature.

The limiting electric current type oxygen sensor of the present invention has an insulating layer on one of the anode and cathode thereof and a heater integrally formed with the insulating film. The insulating film serves to limit the amount of oxygen permeated in an oxygen ionic conductor and to electrically insulate the oxygen ionic conductor from the heater. In order to provide the above functions, the insulating film has a porosity of not less than 0.2 [%], an average pore diameter of not less than 140 [Å], and a thickness range of 0.2 [$\mu$m] to 10 [$\mu$m].

In order to properly determine the amount of permeation of oxygen, a hole is formed in the insulating film to determine the amount of permeation of oxygen, and an area of the hole is preferably determined to be not less than 1/33 of the area of the anode or cathode.

Furthermore, according to the present invention, a constant temperature heating control circuit is used together with the limiting electric current type oxygen sensor to control the temperature of the heater in accordance with the heater resistance and the oxygen ionic conductor resistance, thus obtaining the limiting electric current type oxygen concentration detecting device.

The above and other objects, advantages and features of the present invention will become apparent from the following description of the foregoing and other embodiments thereof presented in conjunction with the accompanying drawings.

DETAILED DESCRIPTION

I. Detailed Description of the Prior Art

Figure 1A:
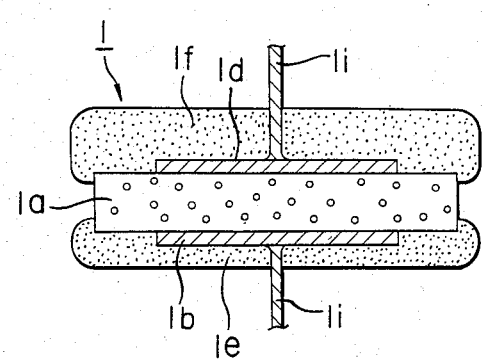
FIG. 1A is a sectional view of a configuration of a limiting electric current type oxygen sensor.

FIG. 1A shows an example of the configuration of a conventional electric limiting electric current type oxygen sensor. An oxygen ionic conductor $1a$ is a plate or a cylinder a material of which is a sintered body of a solid solution containing zirconia ($ZrO_2$) and one or more materials selected from the group including $Y_2O_3$, $Yb_2O_3$, $Gd_2O_3$, MgO, CaO, $Sc_2O_3$ and so on as a stabilizer, a solid solution containing $Bi_2O_3$ and one or more materials selected from the group including $Y_2O_3$, $Er_2O_3$, $WO_3$ and so on as a stabilizer, or a solid solution containing one or more materials selected from $HfO_2$, $ThO_2$ and so on and one or more materials selected from the group including CaO, MgO, $Y_2O_3$, $Yb_2O_3$ and so on as a stabilizer. An anode $1b$ is deposited on one surface of the oxygen ionic conductor $1a$, and a cathode $1d$ is deposited on the other surface thereof. The anode $1b$ and the cathode $1d$ are made of a heat-resistant electron conductor of Pt, Ag, Rh, Ir or Pd, or of an alloy containing one or more of the foregoing metals. These materials are used to decrease a resistance of interfaces between the oxygen ionic conductor 1a and the anode 1b between the oxygen ionic conductor 1a and the cathode 1d. The cathode 1d is covered with a material having pores. FIG. 1A shows a schematic configuration of an example of the limiting electric current type oxygen sensor provided with a porous layer 1f which covers the cathode 1d. The porous layer 1f functions to limit the quantity of oxygen gas flowing toward the cathode 1d. On the other hand, the anode 1b is covered with another porous layer 1e which functions to protect the anode 1b from being contaminated by foreign materials and so on. The porous layers 1f and 1e are made of a heat-resistant inorganic material such as alumina, magnesia, silica, spinnel or mullite. It is preferable that the porous layer 1e has a permeability to gas which is equal to or greater than that of the porous layer 1f. This is because that the porous layer 1f serves to control the quantity of oxygen gas which diffuses from the outside of the porous layer 1f to the oxygen ionic conductor 1a through the cathode 1d, whereas the porous layer 1e serves to expell the oxygen gas from the oxygen ionic conductor 1a through the anode 1b. Each of the anode and cathode has a lead wire 1i which comprises a heat-resistant electron conductor selected from the group consisting of Pt, Ag, Rh, Ir, Pd or the like, or an alloy thereof, as is the material of the anode 1b and the cathode 1d.

Figure 1B:
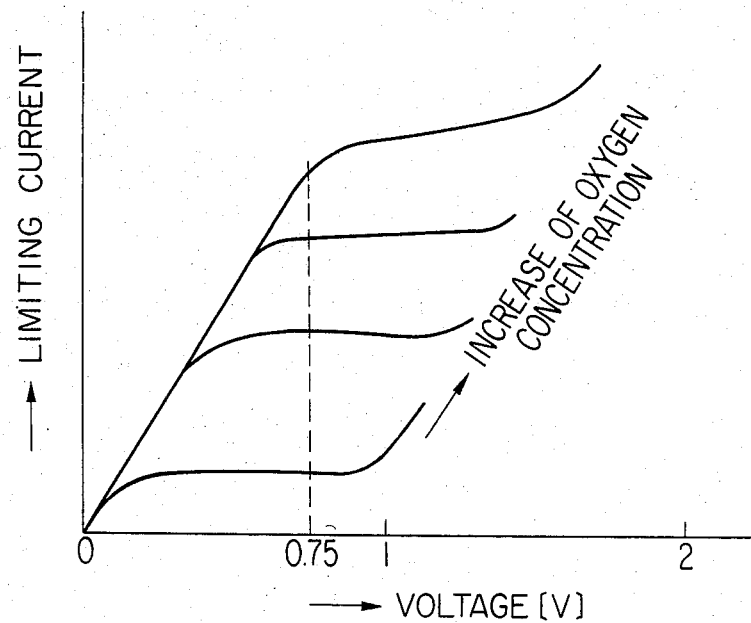
FIG. 1B is a graph showing exemplary voltage-electric current characteristic curves of a limiting electric current type oxygen sensor, using the oxygen concentration as a parameter.

A negative voltage is applied to the cathode 1d and a positive voltage is applied to the anode 1b. Simultaneously, the oxygen sensor is brought into contact with a gas to be measured. The oxygen gas in the gas to be measured is reduced by the cathode 1d to oxygen ions. The oxygen ions flow through the oxygen ionic conductor 1a and reaches the anode 1b. The oxygen ions which have reached the anode 1b are oxidized and converted to oxygen gas again. The oxygen gas is then discharged to the outer atmosphere. If the amount of oxygen gas supplied to the interface between the cathode 1d and the oxygen ionic conductor 1a is limited by a given method, the amount of oxygen ions produced by reduction at the cathode 1d is decreased, thus limiting the flow of charge (electric current) of the oxygen ions. As a result, even if a voltage is increased, only a constant electric current flows, thus obtaining the limiting electric current characteristics, as shown in FIG. 1B. In the limiting electric current characteristics of the oxygen sensor, an electric current is gradually increased at a low voltage substantially in proportion to an increase in a voltage when a voltage is applied across the anode and cathode from zero volts, as shown in FIG. 1B. Such a low-voltage range is called a resistance domination range. However, a constant electric current flows in a certain range independently of a voltage range which is called an overvoltage domination range. The electric current in the overvoltage domination range is called a limiting electric current. The limiting electric current is substantially proportional to the concentration of oxygen in the gas to be measured. If the limiting electric current is detected, the concentration of oxygen in the gas to be measured can be determined. The proportional relationship between the limiting electric current and the oxygen concentration is attributable to the fact that the quantity of oxygen diffused and moved in the gas flow limiter of the porous body is proportional to a difference between the oxygen concentrations inside and outside of the limiter, and that the oxygen concentration is substantially zero in the overvoltage domination range since oxygen inside the limiter is absorbed in the oxygen ionic conductor through the cathode 1d, thus substantially equalizing a difference between the oxygen concentrations inside and outside the limiter to the oxygen concentration outside the limiter.

In the above description, the limiter comprises the porous layer. However, the present invention is not limited to the above arrangement. For example, the cathode itself can be used as a limiter of an oxygen sensor as will be described below. The ratio of voltage to electric current can be determined to be substantially constant by an interface resistance of an electrolyte (oxygen ionic conductor) and a sum of resistances at the interfaces between the electrolyte and the cathode and anode in the resistance domination range. In a range having the voltage and electric current higher than those in the overvoltage domination range, an electric current is abruptly increased even though a voltage is slightly increased. This results from the fact that part of carbon dioxide ($CO_2$) and water vapor ($H_2O$) included in the exhaust gas in a great amount is decomposed when a voltage applied across the limiting electric current type oxygen sensor exceeds a certain limit, thus causing an effect as if the oxygen concentration were actually increased. This range is called as an overcurrent domination range. In fine, when the applied voltage is low, the resistance domination range is obtained. However, when the applied voltage is high, the overcurrent domination range is obtained. Therefore, the limiting electric current must be detected in an intermediate range between the resistance domination range and the overcurrent domination range. The intermediate range varies in accordance with the gas composition and the electrode composition. In an inert gas atmosphere such as nitrogen and argon which partially includes oxygen, the intermediate range falls within a voltage range of 1.3 [V] to 1.6 [V]. However, in a gas such as an exhaust gas which mainly contains carbon dioxide and water vapor and partially contains oxygen, the intermediate range falls within a voltage range of 0.6 [V] to 0.8 [V]. Since the maximum voltage drop across the internal resistance is generally limited to be about 0.5 [V], a voltage applied across the oxygen sensor is set to be 0.6 [V] to 0.75 [V] so as to obtain good results free from adverse effects of the overcurrent.

Figure 2:
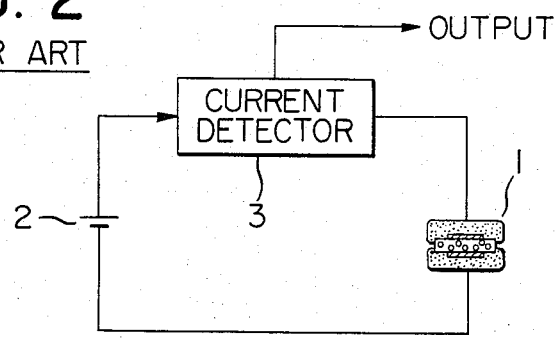
FIG. 2 is a block diagram showing an example of a conventional measuring circuit using a limiting electric current type oxygen sensor.
Figure 3:
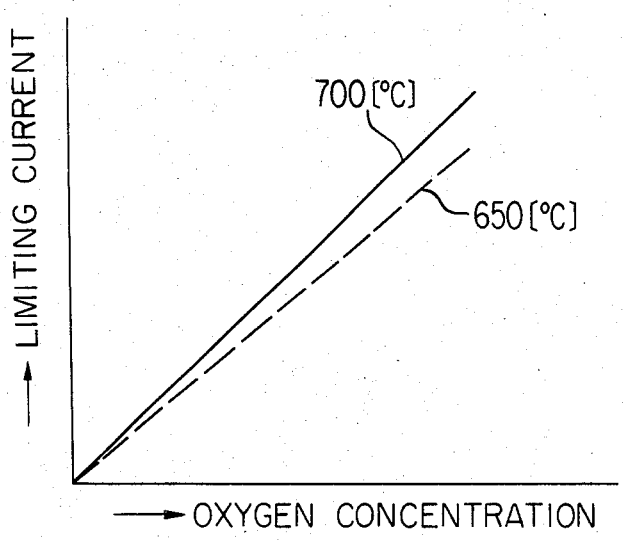
FIG. 3 is a graph for explaining the limiting electric current as a function of the oxygen concentration at two different temperatures.

FIG. 2 shows a conventional limiting electric current measuring circuit. When a constant voltage is applied from a constant power source 2 to a limiting electric current type oxygen sensor 1, an electric current flowing through the oxygen sensor is detected by an electric current detecting device 3. FIG. 3 shows the relationship between the oxygen concentration and the limiting electric current according to the conventional electric current measuring circuit. As may be apparent from FIG. 3, the relationship between the oxygen concentration and the limiting electric current is changed with respect to the temperature of the sensor. Therefore, when the oxygen sensor is used in an atmosphere where the temperature greatly varies, measuring precision is degraded.

Figure 4:
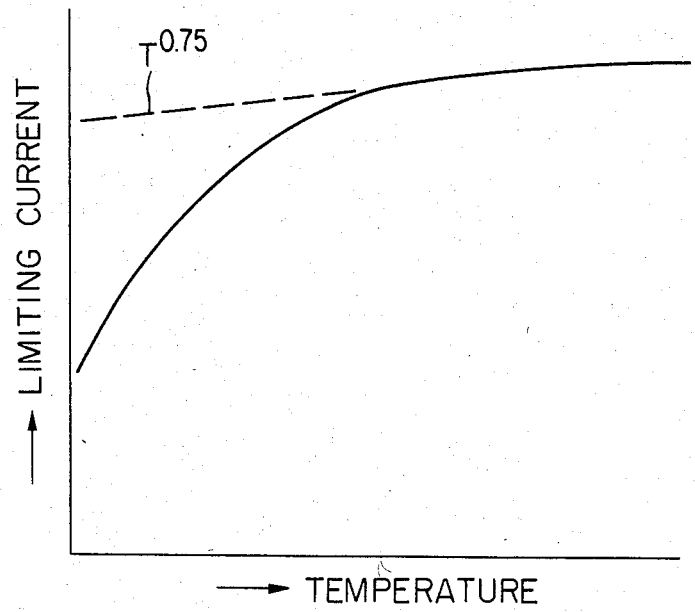
FIG. 4 is a graph for explaining the limiting electric current as a function of the temperature when the oxygen concentration is constant.

FIG. 4 shows dependency of the limiting electric current on the temperature at an arbitrary oxygen concentration. This dependency results from the dependency of the vapor diffusion coefficient on the temperature.

The characteristics of an oxygen sensor having a porous layer which serves to regulate the flow rate of oxygen gas therein is represented by the following equation:

$$I_l = \{(4FSD_{O2eff}P)/RTl\} \cdot \ln[1/\{1-(P_{O2}/P)\}] \quad (1)$$

where
- $I_l$: the limiting electric current
- F: Faraday constant
- S: the area of a member which regulates the flow rate of oxygen gas
- $D_{O2}$: the effective diffusion coefficient
- $P_{O2}$: the partial pressure of oxygen gas
- P: the total pressure
- R: the gas constant
- T: the absolute temperature
- l: the thickness of a porous layer
- ln: natural logarithm If the ratio of the partial pressure $P_{O2}$ to the total pressure P is greatly smaller than 1, the following equation can be approximated:

$$I_l \approx \{(4FSD_{O2eff}P)/RTl\}(P_{O2}/P) \quad (2)$$

$D_{O2eff}$ is experimentally obtained as follows:

$$D_{O2eff(T)} = D_{O2eff(T0)}(T/T0)^{m+1} \quad (3)$$

For the exponent $(m+1) \approx 1.75$ where
- T0: the reference temperature
- $D_{O2eff(T)}$: the effective diffusion coefficient at the temperature T
- $D_{O2eff(T0)}$: the effective diffusion coefficient at the reference temperature T0

The ratio of the output electric current $I_{l(T)}$ at the temperature T to the output electric current $I_{l(T0)}$ at the reference temperature T0 at the same partial pressure of oxygen gas, that is, the dependency of the output electric current on the temperature is given by the following equation:

$$I_{l(T)}/I_{l(T0)} = (T/T0)^m \quad (4)$$

As may be apparent from equation (4) and FIGS. 3 and 4, when the measuring temperature T is changed, the limiting electric current $I_{l(T)}$ is changed, resulting in an error. Therefore, if measurement is performed at the constant temperature, the error can be eliminated.

As described above, since the temperature of the exhaust gas from the internal combustion engine is usually changed, temperature detection and temperature control must be performed to keep the constant temperature.

A heat-sensitive element such as a thermocouple and a heat-sensitive resistor is generally disposed in the vicinity of the limiting electric current type oxygen sensor to detect the temperature. However, such an arrangement presents practical problems such that the limiting electric current type oxygen sensor including the heat-sensitive element becomes complex, large in size, and high in cost. Furthermore, the temperature of the heat-sensitive element is not always equal to that of the limiting electric current type oxygen sensor.

Figure 5:
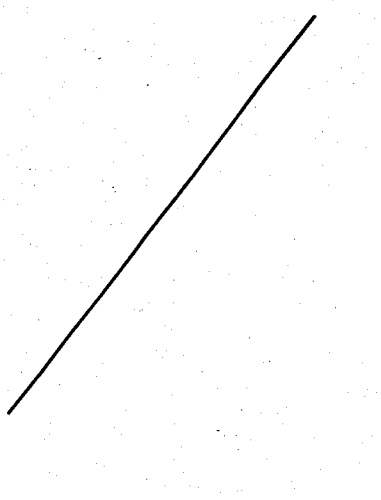
FIG. 5 is a graph for explaining the logarithm of resistivity as a function of the inverse number of the absolute temperature so as to show dependency of the internal resistance on the temperature.

In order to solve the above problems, the present inventors have already proposed a technique in which a temperature is detected using the fact that the internal resistance of the limiting electric current type oxygen sensor is changed in accordance with a change in temperature (FIG. 5), and that the temperature of the limiting electric current type oxygen sensor is kept constant in accordance with the detection of the resistance, in U.S. Ser. No. 373,257 entitled "Equipment for Detecting Oxygen Concentration" filed on Apr. 29, 1982.

Figure 6:
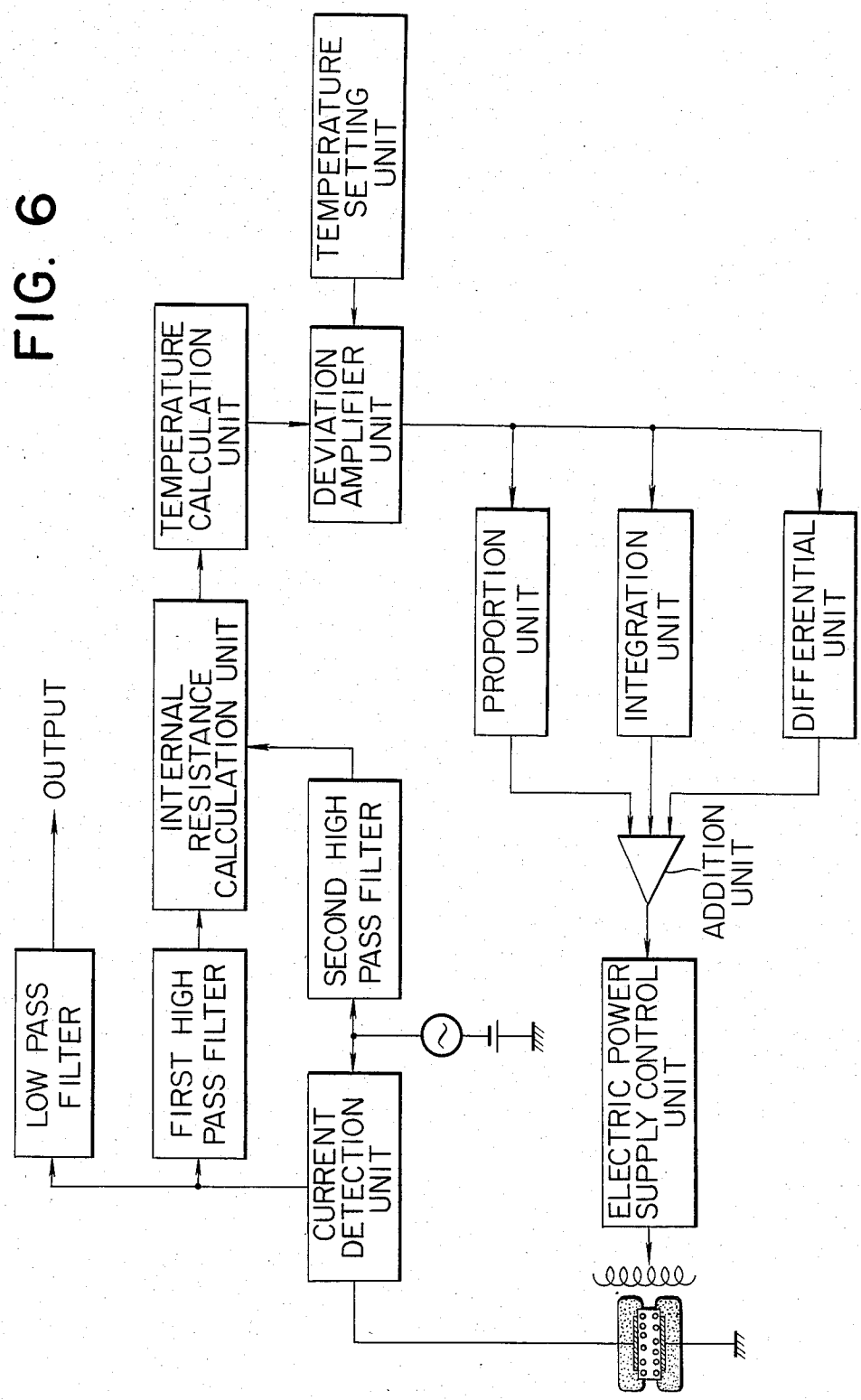
FIGS. 6 to 8 are block diagrams of circuits for maintaining the temperatures of the oxygen sensors constant by detecting temperatures in accordance with the internal resistances of the oxygen sensors, respectively.
Figure 7:
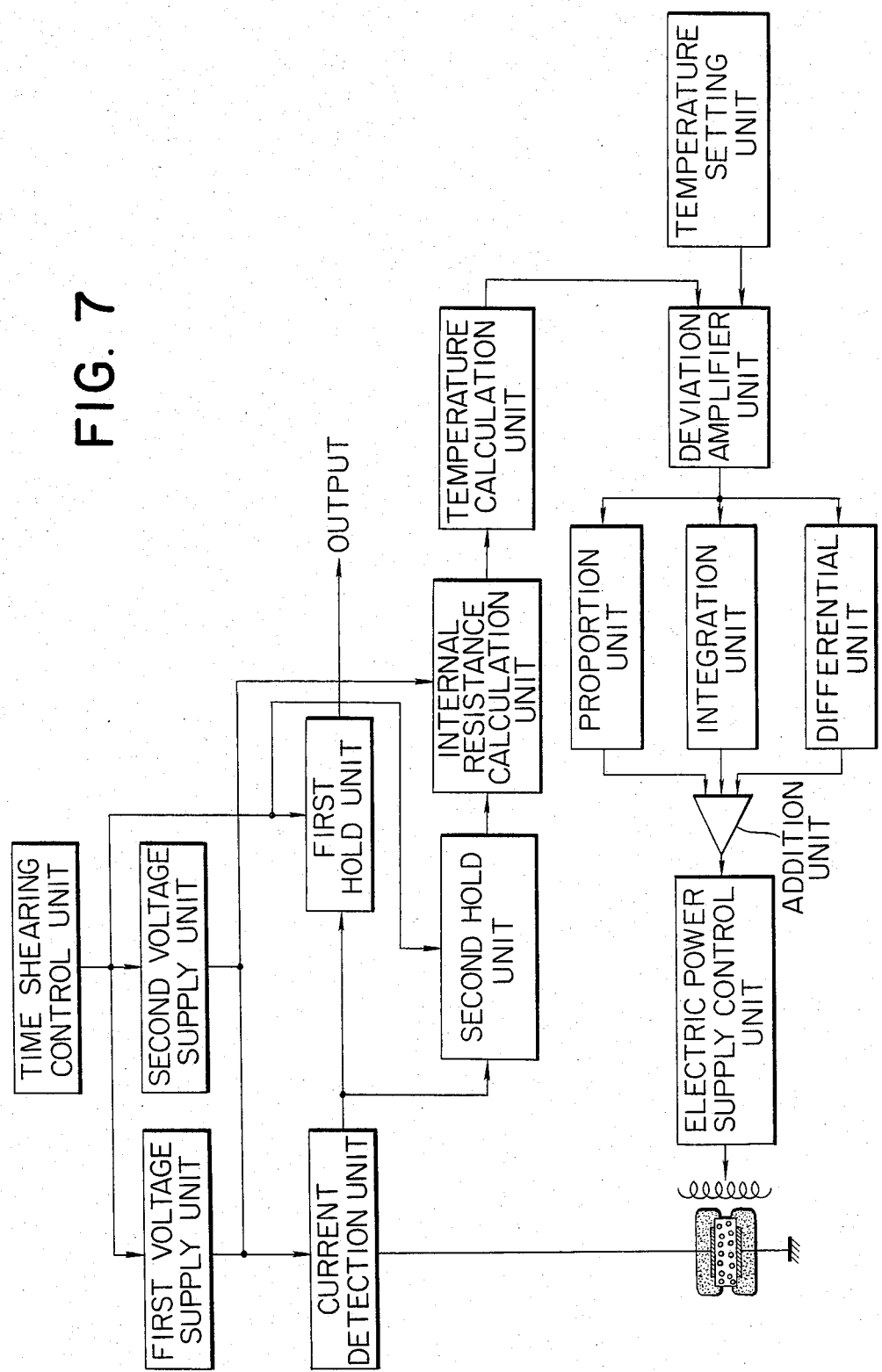
Figure 8:
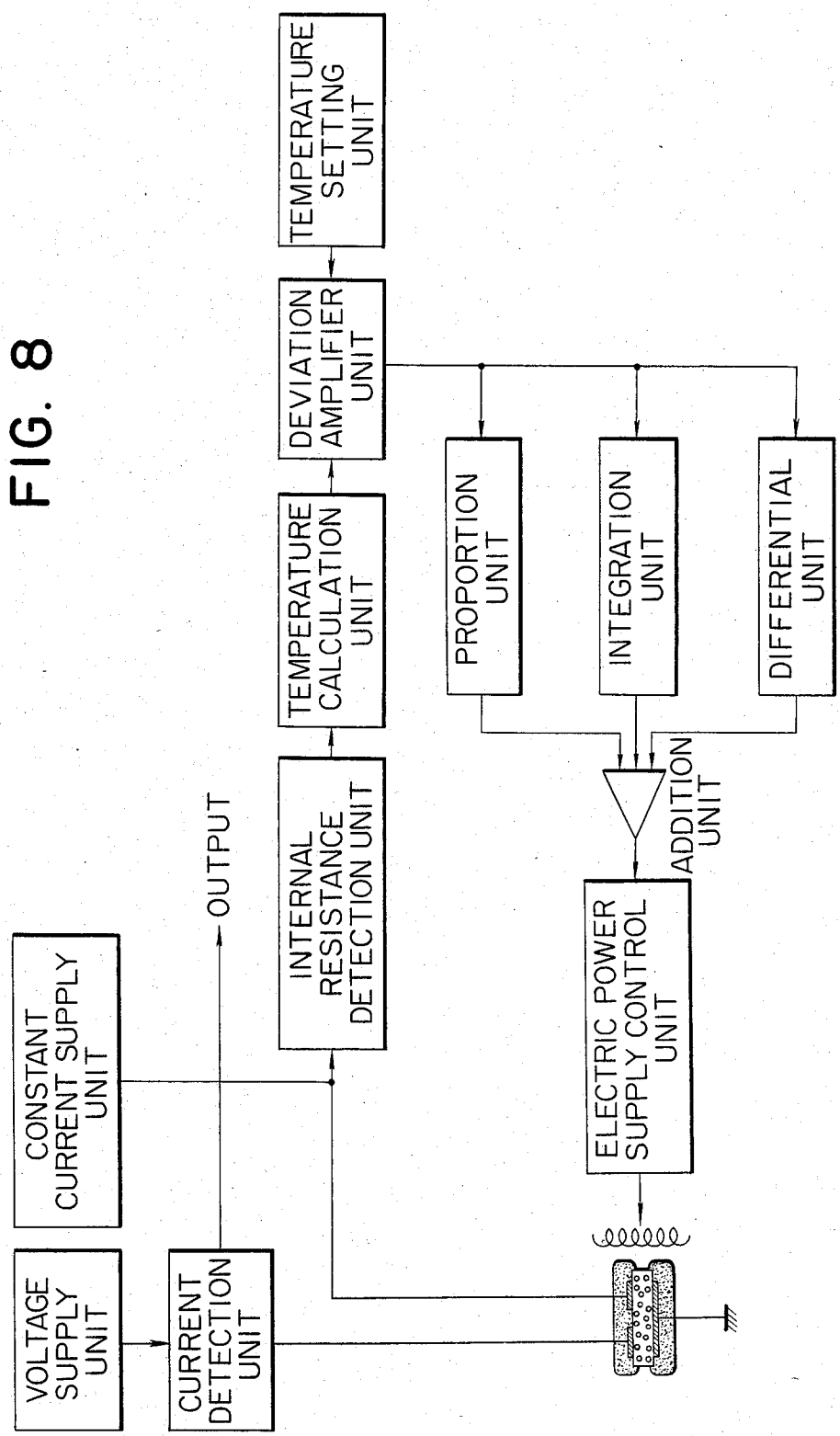
Figure 10A:
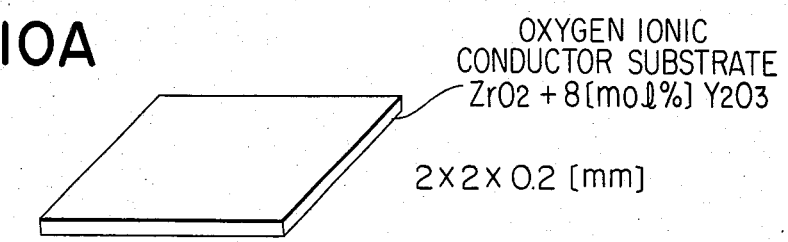
FIGS. 10A to 10D are perspective views for explaining the steps of forming a sample so as to examine the conditions of the insulating film.
Figure 10B:
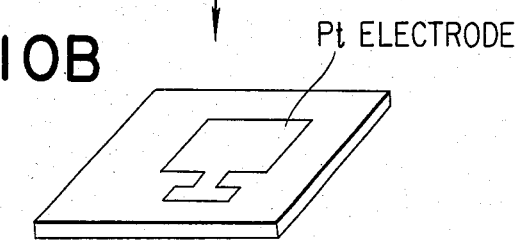
Figure 10C:
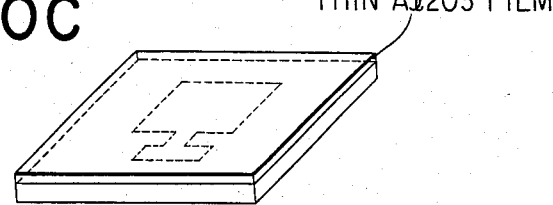
Figure 10D:
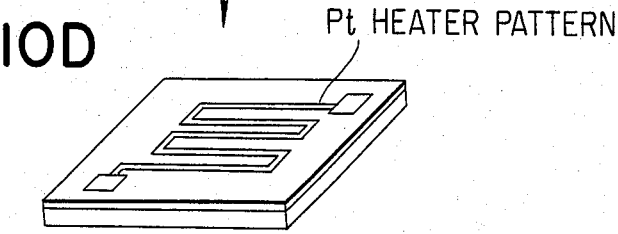

FIGS. 6 to 8 show circuit configurations described in U.S. Ser. No. 373,257, which is effectively utilized, but which has a few problems yet. The power consumption of any sensor mounted in an automobile must be generally not more than several watts. However, the equipment described in U.S. Ser. No. 373,257 and any other conventional oxygen sensor requires power of several tens of watts, resulting in inconvenience. Furthermore, it takes a considerably long period of time before the sensor operates after the switch is turned on in accordance with the following reasons:

(1) Small response time is required for the automobile oxygen sensor since the air velocity around the sensor is very high and the purification rate of the gas is very high.

(2) Since the conventional oxygen sensor has a heater in the vicinity thereof, the heat conduction efficiency is low.

It is noted that the conventional oxygen sensor adopts a heater disposed in the vicinity thereof since the oxygen ionic conductor of the limiting electric current type oxygen sensor is electrically conductive, so that leakage electric current from the heater circuit flows in the measuring circuit to cause much trouble if the heater is formed directly on the oxygen ionic conductor.

II. Detailed Description of the Preferred Embodiment

Figure 9:
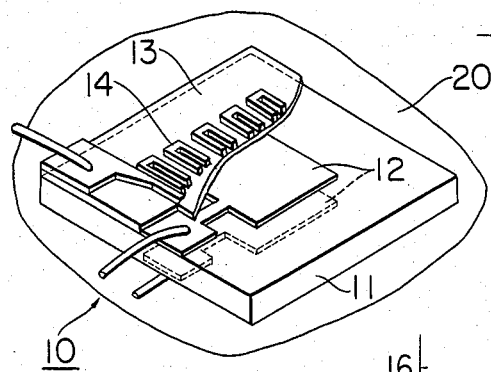
FIG. 9 is a partially cutaway perspective view of a limiting electric current type oxygen sensor according to an embodiment of the present invention.

FIG. 9 shows a limiting electric current type oxygen sensor 10 according to an embodiment of the present invention. Cathode (or anode) and anode (or cathode) 12 are respectively formed on the upper and lower surfaces of an oxygen ionic conductor 11. An insulating film 13 is formed on one of the cathode and anode 12 to provide electrical insulation and to regulate the flow rate of oxygen gas and constitutes a limiting electric current detection section. A heater pattern layer 14 containing platinum as the major component is formed on the insulating film 13 so as to heat the limiting electric current detection section. A porous film 20 is formed to cover the entire surface of the heater pattern layer 14 so as to mechanically protect it.

In the limiting electric current type oxygen sensor in which the limiting electric current detection section is integral with the heater pattern layer 14, the limiting electric current detection section and the insulating film for protecting the heater are very important. The insulating film must serve to supply the oxygen gas to or discharge it from the oxygen sensor while it must electrically insulate the oxygen ionic conductor 11 from the heater pattern layer 14. The following results show proper conditions for providing the electrical insulation and the flow rate regulation of oxygen gas.

(1) Relationships between Thickness of Insulating Film and Leakage Electric Current, between Thickness of Insulating Film and Average Pore Diameter, and between Thickness of Insulating Film and Porosity thereof (a) Formation of Sensor FIGS. 10A to 10D show the steps of forming a sample of a limiting electric current type oxygen sensor.

Pt films each having a thickness of 1 [μm] are deposited on the upper and lower surfaces of an oxygen ionic conductor ($ZrO_2 + 8$ [mol %]$Y_2O_3$) having dimensions of 2×2×0.2 [mm], using a conventional sputtering apparatus, under the conditions specified below:

| Distance between the target and the substrate: | 40 [mm] |
|---|---|
| Ar pressure: | $2 \times 10^{-2}$ [Torr] |
| Applied voltage: | 1500 [V] |
| Electric current: | 100 [mA] |
| Sputtering time: | 40 [min] |
| Substrate heating: | None |

A thin $Al_2O_3$ film is formed by a high-rate sputtering apparatus on one of the surfaces of the conductor under the conditions given below:

| Distance between the target and the substrate: | 40 [mm] |
|---|---|
| Ar pressure: | $3 \times 10^{-3}$ [Torr] |
| Applied voltage: | 2000 [V] |
| Electric Current: | 150 [mA] |

Figure 11:
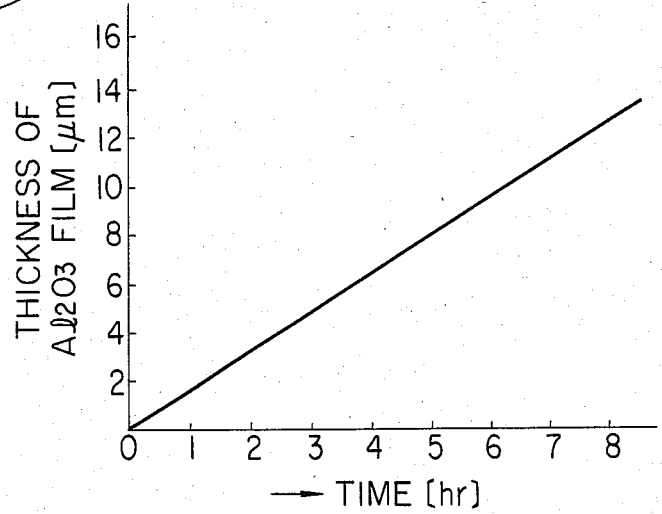
FIG. 11 is a graph for explaining the film thickness as a function of the sputtering time.

The relationship between the sputtering time and the thickness of the $Al_2O_3$ is shown in FIG. 11.

A Pt heater pattern having a thickness of 1 [μm] is formed on the thin $Al_2O_3$ film under the same conditions as in formation of the Pt electrodes. Thus, a sample is manufactured which has a multilayer of the Pt electrode, the $ZrO_2$ substrate, another Pt electrode, the thin $Al_2O_3$ film, and the Pt heater. Pt lead wires each having a diameter of 50 [μm] are bonded by hot pressing on the Pt heater electrode and on the upper and lower surfaces of the oxygen ionic conductor.

(b) Leakage Electric Current Check

A sample which is formed to check whether or not the limiting electric current detection section and the heater are short-circuited is heated to a temperature of about 750 [°C.]. A voltage of 50 [V] is applied across the sample to check the leakage electric current using an ammeter. If a leakage electric current is not more than 20 [μA], the sample is regarded to be satisfactory. However, if the leakage electric current exceeds 20 [μA], it is regarded to be unsatisfactory.

(c) Porosity Measurement

A sodium chloride substrate having dimensions of 20×20×0.3 [mm] is set in the vicinity of a sample on which the thin $Al_2O_3$ film is formed by the sputtering apparatus. The thickness of the sputtered $Al_2O_3$ film is measured using a film thickness measuring gauge manufactured by Tenpole Inc. Thereafter, the sodium chloride substrate is submerged in water so as to remove the $Al_2O_3$ film from the rest of the structure. The $Al_2O_3$ film is then weighed to obtain an apparent specific gravity from the weight and the dimensions (20×20 [mm]) of the $Al_2O_3$ film. Thereafter, the specific gravity of monocrystalline $Al_2O_3$ is defined as a true specific gravity, thus obtaining the porosity ε as follows:

$\epsilon = 1 - (\rho: \text{apparent}/\rho: \text{true})$ where ρ: the specific gravity.

(d) Measurement of Average Pore Diameter

Figure 12:
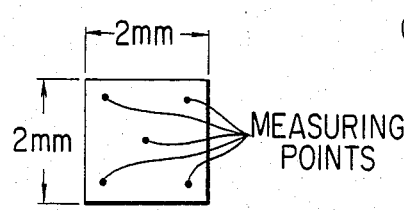
FIG. 12 is a schematic view showing the positions where the pore diameter is measured.

The $Al_2O_3$ film used for porosity measurement is formed into a film portion having dimensions of 2×2 [mm] and the diameters of pores at five points (FIG. 12) within an area of 2×2 [mm] are measured by magnifying them with a magnification of not less than 100,000 times using an electron microscope. The average pore diameter is then obtained.

(e) Results

The results of the above measurements are summarized in Table 1.

TABLE 1

Relationships among Sputtered $Al_2O_3$ Film Thickness, Leakage Electric Current, Average Pore Diameter, and Porosity

| $Al_2O_3$ film thickness [μm] | 0.12 | 0.2 | 0.6 | 0.75 | 2.3 | 5.8 | 8.3 | 10.4 |
|---|---|---|---|---|---|---|---|---|
| Leakage electric current | yes | yes | none | none | none | none | none | none |
| Average pore diameter of $Al_2O_3$ film [Å] | 340 | 230 | 190 | 190 | 170 | 160 | 150 | 140 |
| Volume porosity [%] | 9.8 | 7.3 | 3.1 | 2.6 | 0.5 | 1.0 | 1.5 | 0.2 |
| Evaluation | x | x | o | o | o | o | o | Δ | o: good
Δ: fair
x: poor

Figure 13:
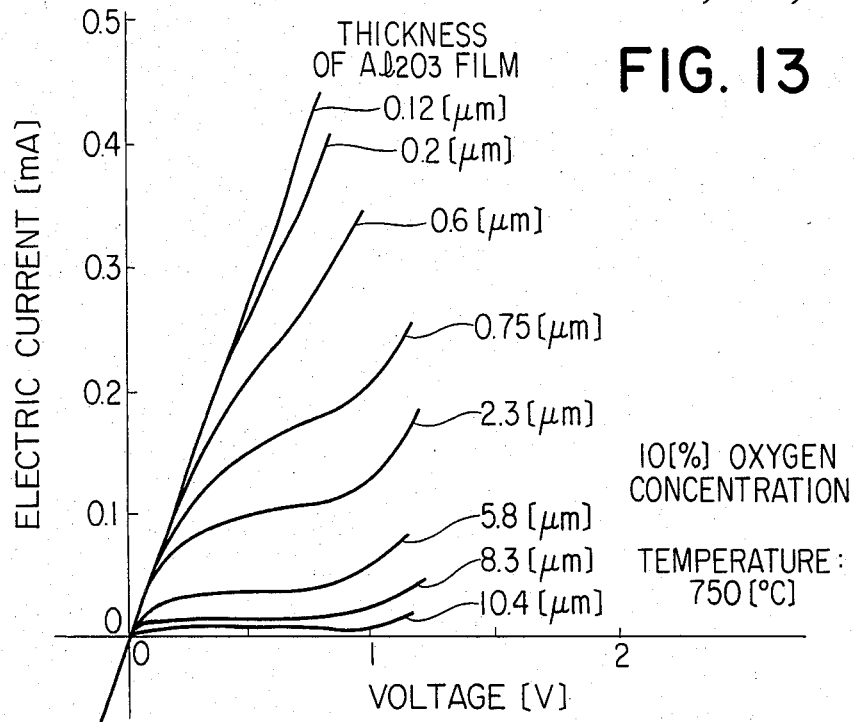
FIG. 13 is a graph showing the voltage-electric current characteristic curves, using as a parameter the thickness of the $Al_2O_3$ insulating film for controlling oxygen gas permeation.
Figure 14:
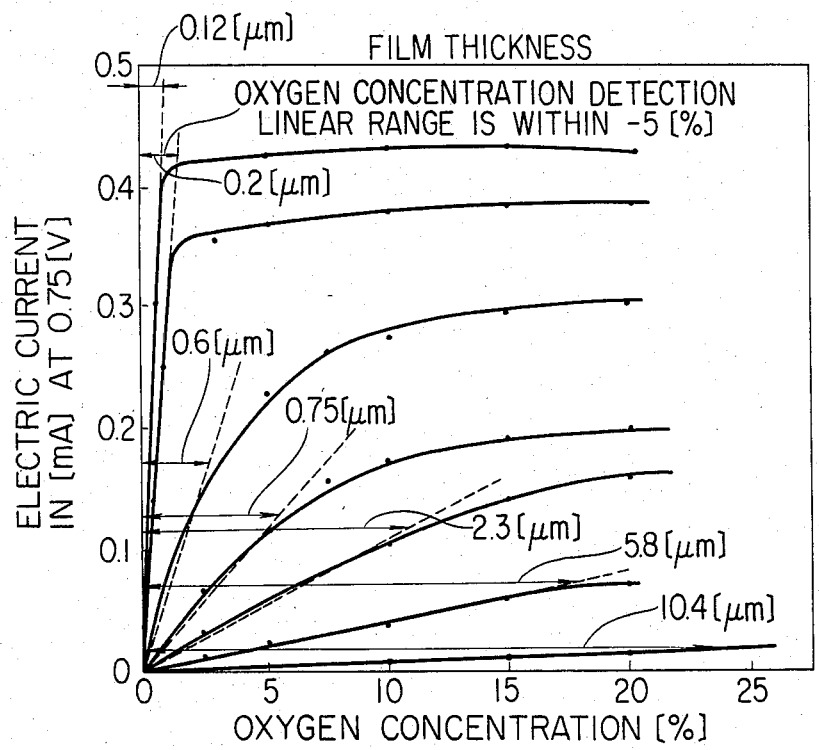
FIG. 14 is a graph for explaining the sensor output electric current at a voltage of 0.75 [V] as a function of the oxygen concentration, using the $Al_2O_3$ insulating film thickness as a parameter.
Figure 15A:
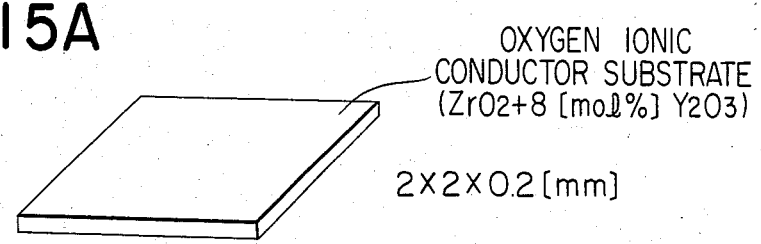
FIGS. 15A to 15D are perspective views for explaining the steps of forming a sample so as to examine a hole diameter for controlling the constant permeation of oxygen.
Figure 15B:
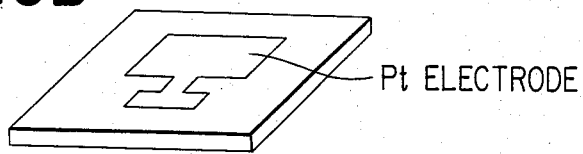
Figure 15C:
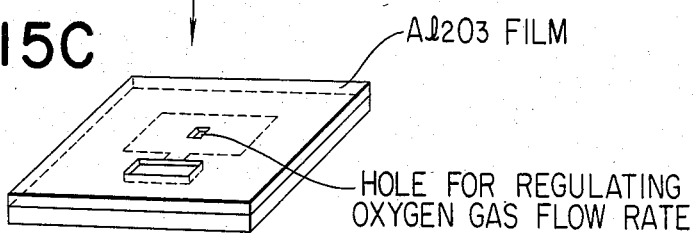
Figure 15D:
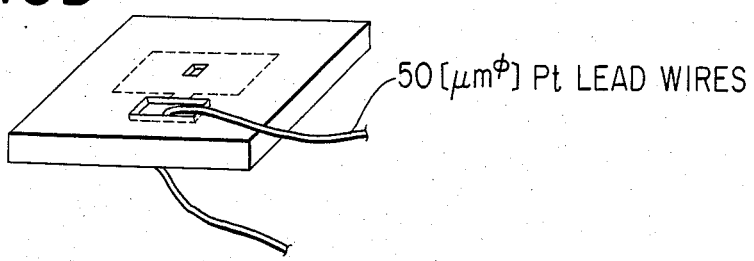

In order to test the limiting electric current characteristics of the sample, the sample is heated from its side surface by a sheath heater at a temperature of 750 [°C.] in an atmosphere of a mixture of nitrogen and oxygen gases having an oxygen concentration of 10 [%] so as to examine the voltage-electric current characteristics. Results are shown in FIG. 13. The sensor output electric current is plotted along the axis of ordinate when a voltage of 0.75 [V] is applied across the sample, whereas the oxygen concentration is plotted along the axis of abscissa, as shown in FIG. 14. An oxygen concentration is checked at which the oxygen concentration detection linear characteristic is deviated by −5 [%]. The oxygen concentration detection linear range is widened when the film thickness is increased, as shown in FIG. 14. However, the detection electric current is inversely proportional to the oxygen concentration detection linear range. From the results of Table 1, and FIGS. 13 and 14, the film thickness must be not less than 0.2 [μm] in order to provide electrical insulation. However, as may be apparent from FIGS. 13 and 14, when the film thickness is not less than 10 [μm], permeability to oxygen gas is degraded, and a small amount of electric current flows even though a voltage is applied. In fine, in a thin film formed by physical thin film formation method (vacuum deposition or sputtering), the film thickness must fall within a range of 0.2 [μm] to 10 [μm] so as to satisfy both electrical insulation and regulation of oxygen gas. The average pore diameter is preferably not less than 140 [Å], and the volume porosity is preferably not less than 0.2 [%].

In the above example, the conditions have been described for forming the thin $Al_2O_3$ film. In the same manner as described above, a thin film can be formed by a heat-resistant inorganic material such as $SiO_2$, silica, spinnel, and magnesia. When the electrical insulation and permeability to oxygen gas of the thin film obtained above are examined, the same conditions as in formation of the thin $Al_2O_3$ film can be substantially applied.

(2) Relationship between Area of Limiting Electric Current Detection Section and Area of Hole Formed in Insulating Film As described above, the insulating film must serve to electrically insulate the heater from the limiting electric current detection section and to supply oxygen gas to or exhaust it from the limiting electric current detection section. In order to properly regulate the flow rate of oxygen gas through the limiting electric current detection section, a proper hole must be formed therein. The conditions for the hole area are thus examined.

A limiting electric current type oxygen sensor as a sample to determine the conditions for the hole formed in the insulating film is formed by vacuum deposition or sputtering. FIGS. 15A to 15D show the steps of manufacturing the limiting electric current type oxygen sensor. Pt electrodes each having a thickness of 1 [μm] have the same area and are formed as the anode and cathode on the upper and lower surfaces of an oxygen ionic conductor substrate ($ZrO_2 + 8$ [mol %] $Y_2O_3$). A thin $Al_2O_3$ which has excellent electrical insulation is formed on one of the surfaces to a thickness of 8.5 [μm]. The Pt electrodes and the thin $Al_2O_3$ film are formed in the same manner as in FIGS. 10A to 10C. Thereafter, a hole is formed in a portion of the $Al_2O_3$ film which corresponds to the electrode, using hydrogen fluoride. Pt lead wires each having a diameter of 50 [μm] are bonded on the cathode and anode electrodes of the oxygen ionic conductor.

Figure 16:
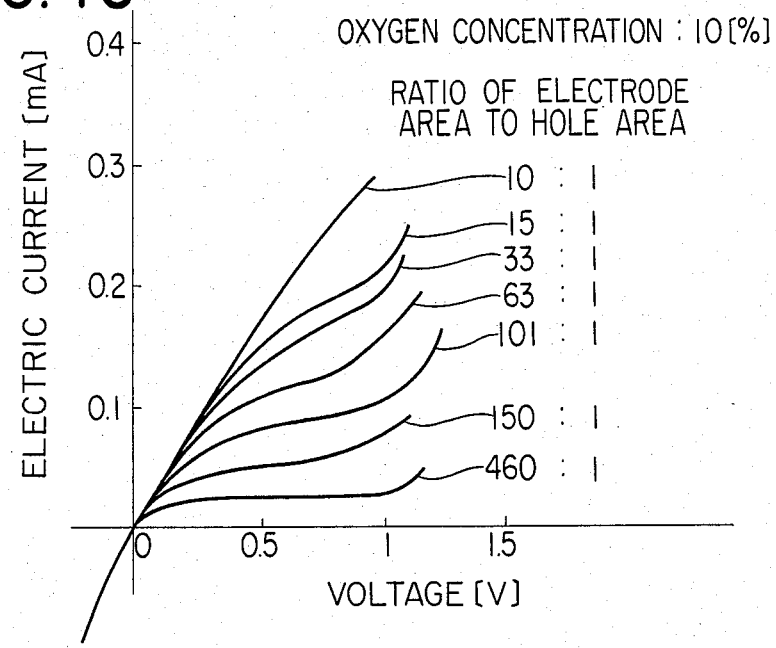
FIG. 16 is a graph showing the voltage-electric current characteristic curves when the ratio of the area of the electrode used for detecting a limiting electric current to the area of the hole formed in the insulating film is used as a parameter.
Figure 17:
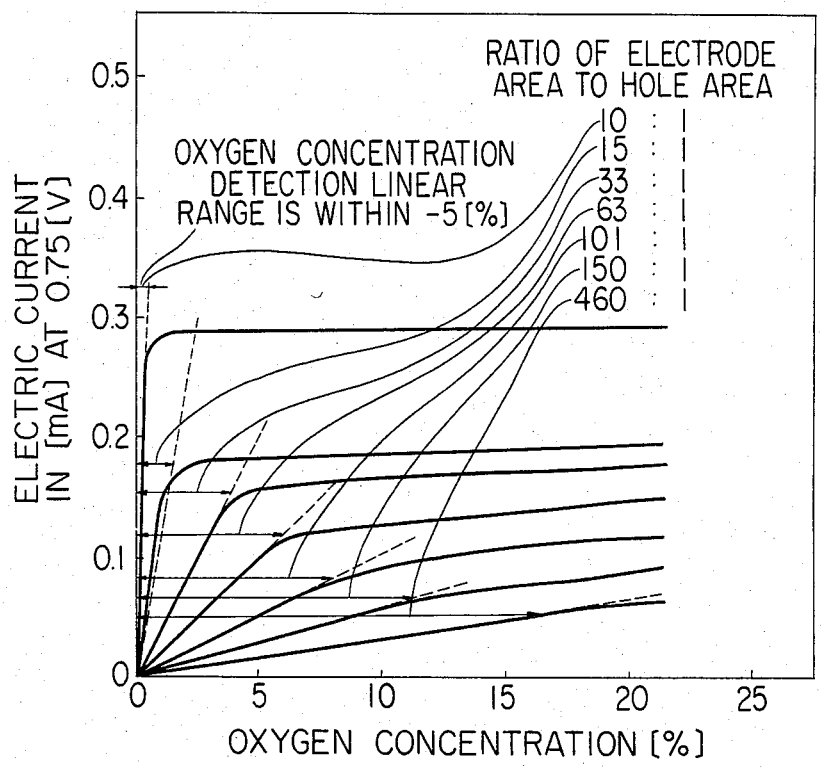
FIG. 17 is a graph for explaining the sensor output electric current at a voltage of 0.75 [V] as a function of the oxygen concentration.

A set of samples respectively having holes of different sizes are prepared in the same process as described above. Limiting electric current characteristics are then examined at an oxygen concentration of 10 [%], using as a parameter the ratio of the hole area to the area of the electrode. It is noted that the samples are heated from their side surfaces by a sheath heater to a temperature of about 750 [°C.]. Results are shown in FIGS. 16 and 17.

According to these results, when the ratio of electrode area to the hole area is not less than 101:1, the electric current is not so increased even though the voltage is increased. In practice, when the ratio of the electrode area to the hole area is not less than 33:1, the electric current is proportional to the voltage at an oxygen concentration of not more than about 4 [%]. As a result, the sample can be used as an air-fuel ratio sensor.

In the above example, the conditions have been described for forming the thin $Al_2O_3$ film. In the same manner as described above, a thin film can be formed by a heat-resistant inorganic material such as $SiO_2$, silica, spinnel, and magnesia. When the relationship between the electrode area and the hole area of the film obtained above are examined, the same conditions as in formation of the thin $Al_2O_3$ film can be substantially applied.

(3) Stability and Durability of Heater Material

An oxygen sensor is used in which a limiting electric current detection section has Pt anode and cathode of the oxygen ionic conductor and a Pt heater is integral with the limiting electric current detection section which is then heated. Each of the electrodes comprises platinum to which 10 [%] of Rh is added, and has a thickness of 1.2 [μm]. The heater is made of the same material as the electrode and has a thickness of 1 [μm].

Figure 18:
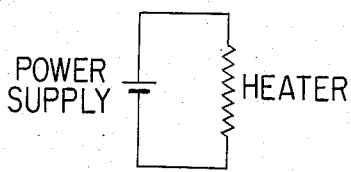
FIG. 18 is a circuit diagram of a circuit for examining the durability of the heater.

In order to examine a change of Pt type material over time, Rh is added to Pt. The resultant alloy is formed into a thin heater layer (thickness of 1 m) and width of 50 [μm]) by the sputtering apparatus. The obtained heater is heated to a temperature 1000 [°C.] and a change thereof over time is examined. As shown in FIG. 18, the heater is heated to a temperature of 1000 [°C.] while the power supplied thereto is controlled and the heater temperature is measured by a pyrometer. A time interval is measured which is required for the heater temperature decrease from 1000 [°C.] to 990 [°C.] when the heater is kept at a temperature of 1000 [°C.] for a long period of time and when it is degraded and its resistance is increased.

TABLE 2

Relationship between Rh content in Pt Alloy and Time Interval required for Heater Temperature to Decrease from 1000 [°C.] to 990 [°C.]

| Rh content [wt %] | 0 | 5 | 18 | 30 | 45 | 60 |
|---|---|---|---|---|---|---|
| Time interval [min.] for heater temperature to decrease by 10 [°C.] | 9 | 15 | 25 | 60 | 120 | 180 |
| Evaluation | | | poor→good | | | |

Figure 19:
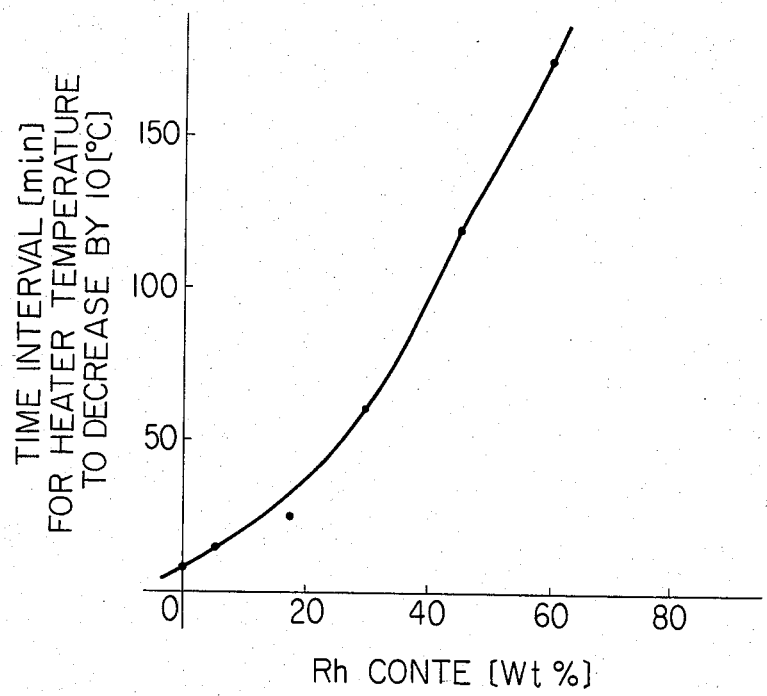
FIG. 19 is a graph for explaining a time interval during which the heater temperature is dropped by 10 [°C.] as a function of the Rh content of the heater.

Results obtained are shown in Table 2 with reference to FIG. 19. As may be apparent from Table 2 and FIG. 19, when the Rh content is increased, the stability of the heater is improved. However, when the Rh content exceeds 60 [wt %], welding characteristic between the Pt lead wires the Pt heater is degraded. As a result, the Rh content of the Pt alloy preferably falls in a range of 0 [wt %] to 60 [wt %].

A method for manufacturing a limiting electric current type oxygen sensor with a microheater according to the present invention will be described with reference to FIGS. 20A to 20G.

Figure 20:
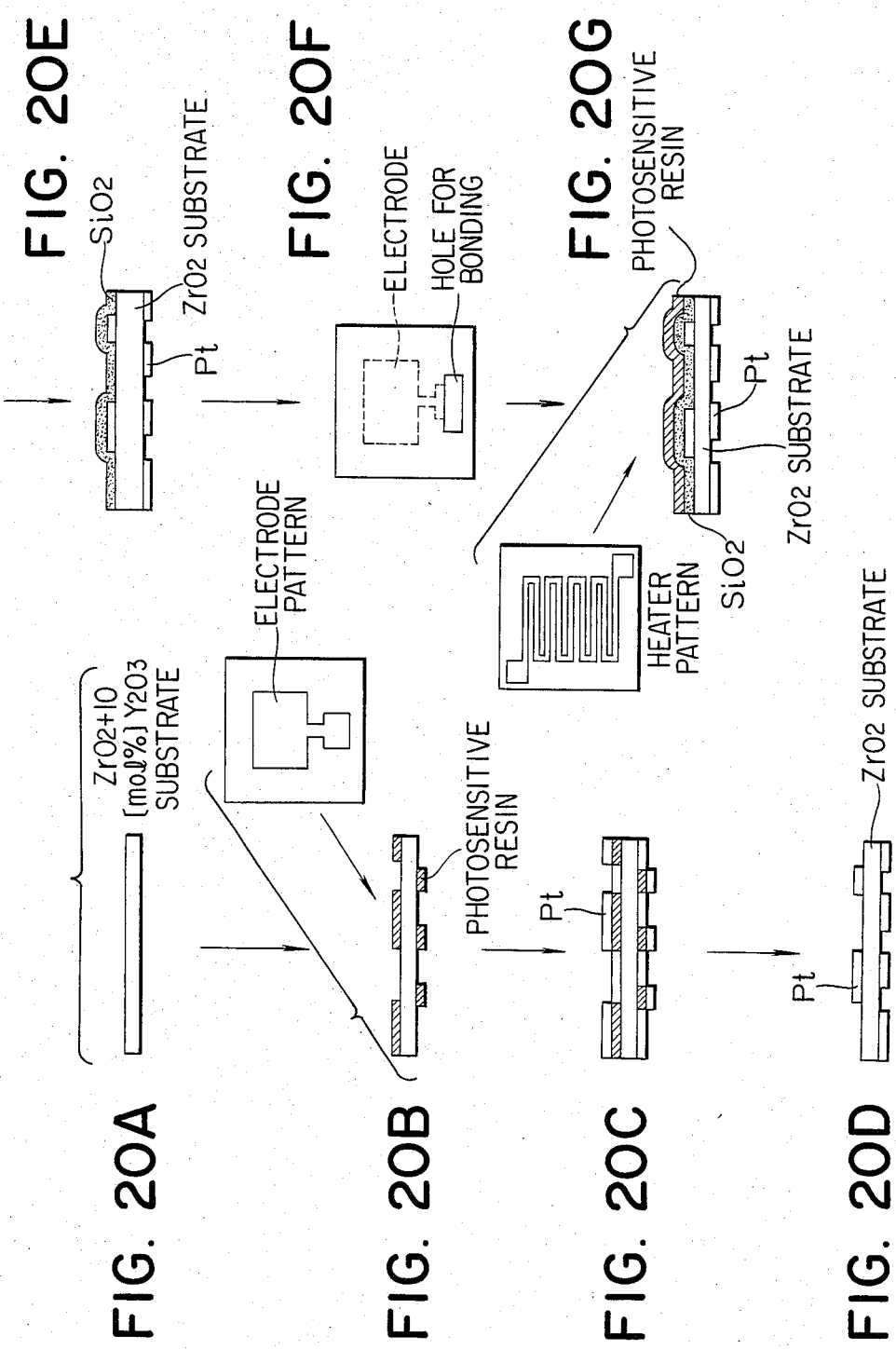
FIGS. 20A to 20G are sectional views for explaining of the steps of manufacturing a limiting electric current type oxygen sensor according to the present invention.
Figure 21:
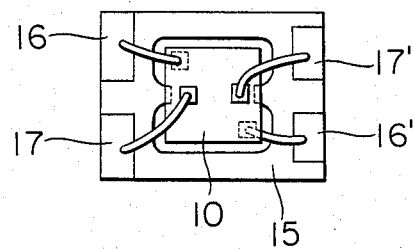
FIG. 21 is a plan view showing a structure in which a sensor is mounted on a base.
Figure 22:
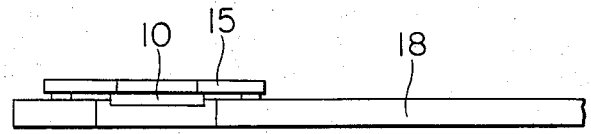
FIG. 22 is a side view showing a structure in which the base is mounted on a sensor holder.
Figure 23:
FIGS. 23 and 24 are a side view and a plan view of the sensor holder as a whole, respectively.
Figure 24:
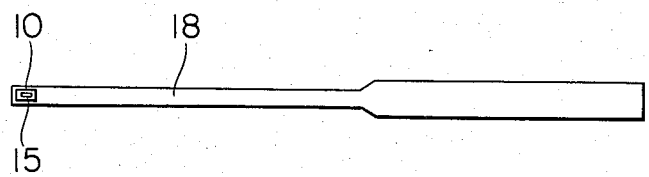

(a) $ZrO_2$ and $Y_2O_3$ powders are mixed, calcined, granulated and press-sintered according to a series of ceramic techniques to form a $ZrO_2 + 10$ [mol %] $Y_2O_3$ substrate (about 17 [mm]$\phi \times 0.2$ [mm]; FIG. 20A).

(b) A photosensitive resin is coated on the upper and lower surfaces of the $ZrO_2$ substrate so as to form Pt electrodes. A portion except for the prospective electrode regions is exposed with light and photopolymerized. As a result, only a portion of the $ZrO_2$ substrate which corresponds to the electrode pattern is exposed (FIG. 20B).

(c) Pt is sputtered on the exposed portions of the upper and lower surfaces of the $ZrO_2$ substrate, using the conventional sputtering apparatus. The $ZrO_2$ substrate is placed in an Ar atmosphere at a pressure of $2 \times 10^{-2}$ [Torr] for 40 [min] at a voltage of 1500 [V] and an electric current of 100 [mA], so that a Pt film having a thickness of about 1 [μm] is deposited on each of the two surfaces (FIG. 20C).

(d) The sputtered substrate is then dipped in an acetone solvent to dissolve the photosensitive resin. As a result, Pt sputtered on the photosensitive resin is removed, and Pt is left only on the exposed portion of the $ZrO_2$ substrate (FIG. 20D).

(e) An $SiO_2$ film is sputtered on one of the two surfaces to electrically insulate the heater from the $ZrO_2$ substrate under the following conditions, using the high-rate sputtering apparatus (FIG. 20E).

| | |
|---|---|
| Pressure in Ar atmosphere: | $3 \times 10^{-3}$ [Torr] |
| Applied voltage: | 2000 [V] |
| Electric Current: | 150 [mA] |
| Sputtering time: | about 30 minutes |

| (Thickness of SiO₂ film: | about 7500 [Å]) |

(f) In order to bond Pt lead wires on the electrode formed under the SiO₂ film, a photosensitive resin is coated on a portion where the Pt lead wires are bonded, in the same manner as in step (b). The coated portion of the SiO₂ film is exposed and etched by hydrofluoric acid to form a hole in the SiO₂ film (FIG. 20F).

(g) A heater is formed on the SiO₂ film in the following manner to be integral with the limiting electric current detection section (FIG. 20G).

A photosensitive resin is coated on the SiO₂ film, and the heater pattern is adhered thereon. In this case, the heater pattern must be free from photopolymerization. When the SiO₂ film is developed, a portion of the SiO₂ film which corresponds to the heater pattern is exposed.

Pt is then deposited on the SiO₂ film to a thickness of about 1 [μm] in the same manner as in step (c).

(h) The resultant sample is cut into pieces each having dimensions of 1.7 [mm]×1.75 [mm], using a dicing machine.

(i) The photosensitive resin is dissolved in acetone solvent to eliminate Pt on the photosensitive resin.

(j) Pt lead wires are bonded on the upper and lower electrodes on the ZrO₂ substrate and the heater electrodes.

(k) The prepared oxygen sensor has a structure shown in FIG. 9. Since the oxygen sensor 10 is difficult to handle as it is, the oxygen sensor 10 is mounted on a base 15 shown in FIGS. 21 to 24. The base 15 is then mounted on a holder 18. The oxygen sensor 10 must be adhered by an Al₂O₃-type adhesive (e.g., trade name: Sumiseram) so as to prevent permeation of oxygen gas. Thereafter, the oxygen sensor 10 is entirely coated with the porous film 20. It is noted that reference numerals 16, 16', 17 and 17' denote terminals, respectively.

The characteristics of the prepared heater and the limiting electric current type oxygen sensor with a heater will be described.

Figure 25:
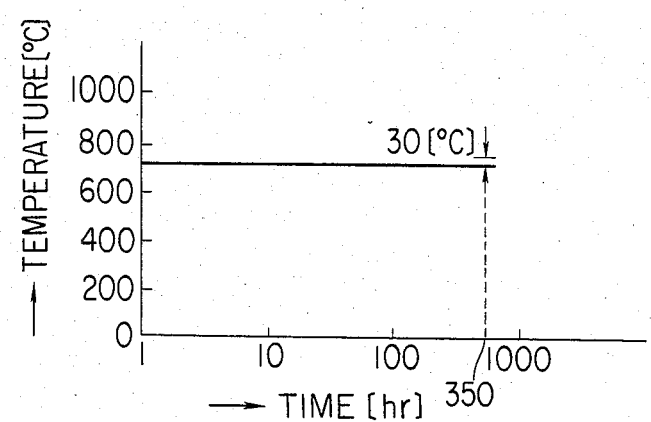
FIG. 25 is a graph for explaining the heater temperature as a function of time so as to show stability of the heater when the heater is continuously heated at a temperature of 740 [°C.]

FIG. 25 shows stability of the Pt heater in a continuous conduction test when a constant voltage is applied thereacross and is heated to a temperature 740 [°C.] in an atmosphere. After the voltage is continuously applied across the Pt heater for 350 hours, the heater temperature is about 710 [°C.], which is 30 [°C.] lower than the initial temperature. As may be apparent from the above test, the Pt heater has stability for a long period of time.

Figure 26:
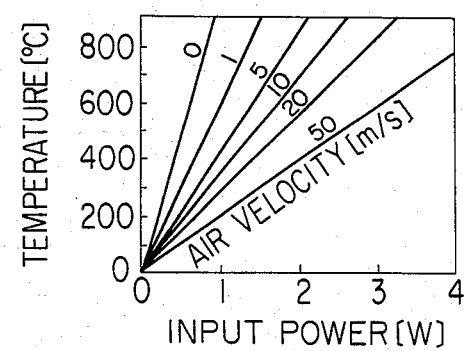
FIG. 26 is a graph for explaining the heater temperature as a function of the input power, using the air velocity as a parameter.
Figure 27:
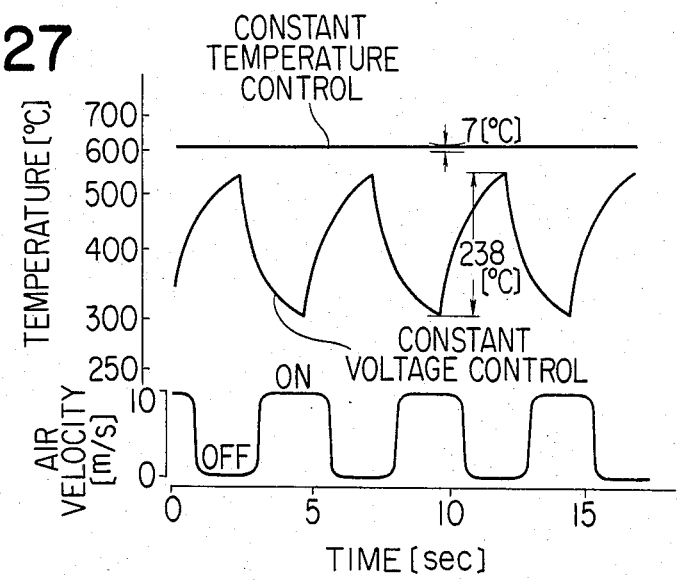
FIG. 27 is a graph showing a change in sensor temperature when the air velocity is alternately changed between zero and 10 [m/s]

FIG. 26 shows the relationship between the heater power and temperature of the sensor shown in FIG. 9. As may be apparent from FIG. 26, input power is changed in a range between 0.5 [W] and 3.5 [W] so as to keep the heater temperature at 700 [°C.] in accordance with the air velocity. The heater temperature is kept at 600 [°C.], using a constant temperature control circuit, while the air velocity is switched between 0 and 10 [m/s] every two seconds. FIG. 27 shows constant temperature control characteristics. As may be apparent from FIG. 27, if the constant temperature control is not performed, the temperature variation corresponds to 238 [°C.] (peak-to-peak). However, if the constant temperature control is performed, the temperature variation is kept within 7 [°C.].

Figure 28:
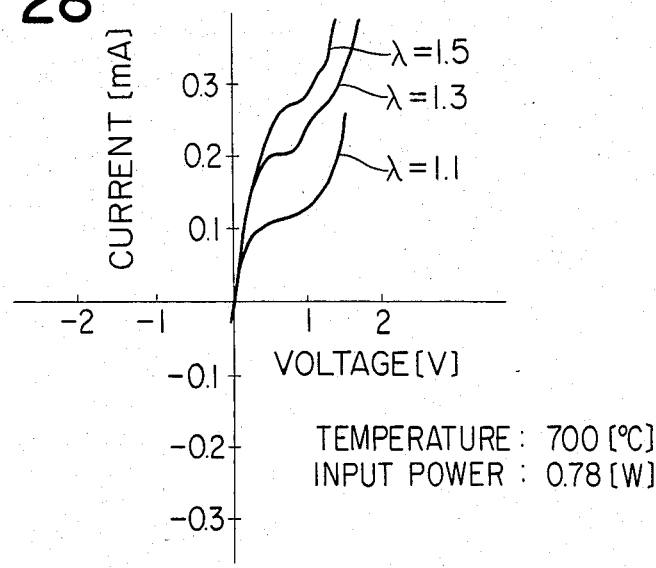
FIG. 28 shows a graph showing the voltage-electric current characteristic curves when the excess air factor $\lambda$ at a heater temperature of about 700 [°C.] (with the heater input power of 0.78 [W]) is used as a parameter.
Figure 29:
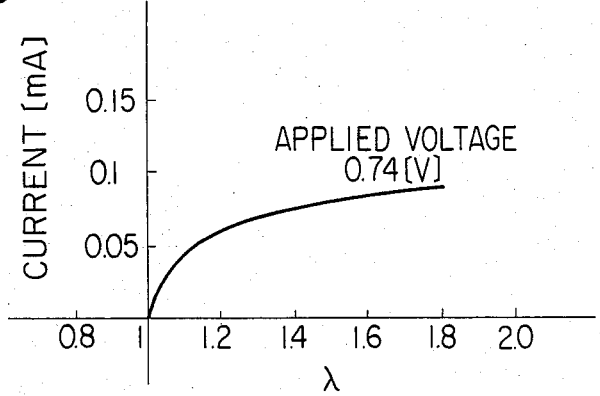
FIG. 29 is a graph for explaining the electric current at voltage of 0.74 [V] as the function of the excess air factor $\lambda$.

FIG. 28 show the voltage-electric current characteristic curves of the limiting electric current type oxygen sensor with a microheater when the heater is heated to a temperature of about 700 [°C.] (with the heater power of 0.78 [W]) and the excess air factors λ is selected to be 1.1, 1.3 and 1.5. FIG. 29 shows the relationship between the electric current and the excess air factor λ constant voltage of 0.74 [V] is applied across the oxygen sensor. As may be apparent from FIGS. 28 and 29, it is found that an electric current flowing through the oxygen sensor is changed in accordance with a change in the excess air factor λ. Furthermore, according to the oxygen sensor of the present invention, since the sensor is integral with the heater, only a power of 0.78 [W] is required to heat the oxygen sensor.

Figure 30:
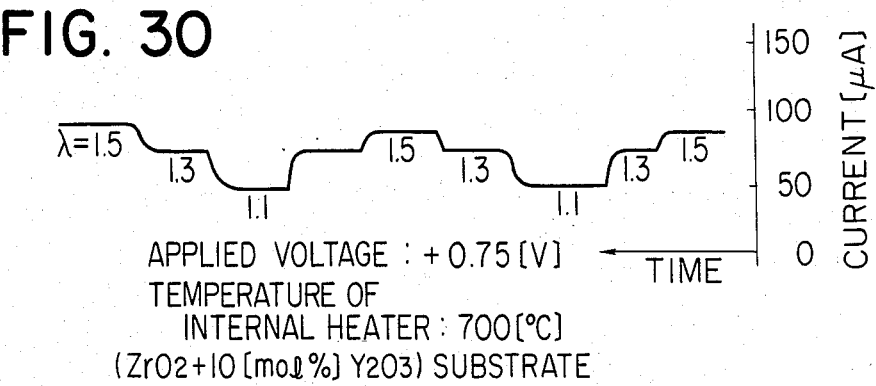
FIG. 30 is a graph showing the response time of the sensor output electric current with respect to a change in the excess air factor $\lambda$.

FIG. 30 shows a change in sensor electric current in accordance with a change in air excess factor λ when a constant voltage of 0.75 [V] is applied across the oxygen sensor. As a result, the oxygen sensor according to the present invention has stable and reproduceable characteristics.

In the above embodiment, Pt or an alloy of Pt and Rh is used as a material of the heater. However, tungsten (W), Kanthal (trade mark), nichrome or the like may also be used as the heater material. In this case, the resistance to corrosion of the latter material is lower than that of the former material, so that a dense protective layer must be formed on the electrode.

When nichrome is used, a change in resistance with respect to a change in temperature is small, so that another heat-sensitive element (e.g., thermocouple and heat-sensitive resistor) may be used to detect a temperature. Instead of detecting the temperature by the separate heater resistance, it is very effective to detect the temperature using the internal resistance of the electrolytic solid material. This method is described in U.S. Ser. No. 373,257 entitled "Equipment for detecting oxygen concentration".

In order to eliminate any variation in the flow rate and temperature of the gas to be measured when the limiting electric current type oxygen sensor with a microheater is used, the temperature must be detected by a heat-sensitive element and must be controlled. When a Pt heater is used, it may not be oxidized at a temperature of not more than 800 [°C.], so that the deterioration of the heater over time is small, and the change in resistance with respect to the change in temperature is large. Therefore, the heater temperature can be obtained by the heater resistance, thus allowing omission of a separate heat-sensitive element In this case, the sensor configuration can be simplified, thus resulting in low cost. Furthermore, since a detection delay can be prevented, an error due to a temperature difference is eliminated. However, a special measure must be taken to prevent interference between the two functions, heating and temperature detection.

Figure 31:
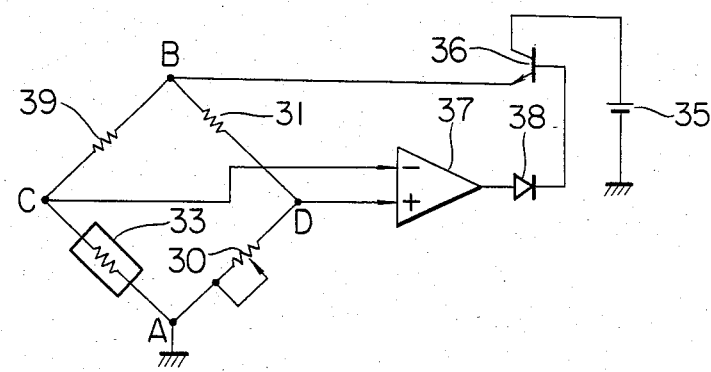
FIG. 31 is a circuit diagram showing an example of a constant heating control circuit allowing heating of the oxygen sensor to a predetermined temperature.

FIG. 31 shows a constant temperature control circuit with a Wheatstone bridge for detecting a temperature by a resistance of the heater and for supplying power for heating. Referring to FIG. 31, a heater 33 is arranged between terminals C and A of the bridge. A voltage from a constant voltage source 35 is applied across terminals B and C of the bridge through a power control transistor 36. An unbalanced voltage across the terminals C and D of the bridge is detected and amplified by a differential amplifier 37 and is applied to the base of the power control transistor 36. In this circuit, a rectifying diode 38 is connected between the base of the power control transistor 36 and the output of the differential amplifier 37, so as to prevent a breakdown in the collector-base path. When the products of resistances of resistors at opposing sides of the bridge become equal, that is, when the product of the resistances of a resistor 39 and a potentiometer (variable resistor) 30 is equal to that of the resistances of a resistor 31 and the heater 33, the unbalanced voltage of the bridge becomes zero, so that constant power is applied across the heater 33 and the sensor temperature is kept constant.

Figure 32:
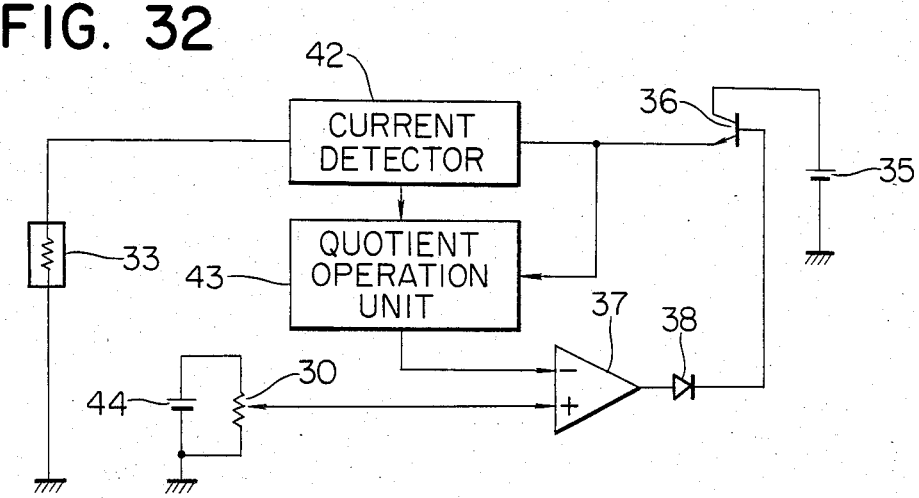
FIG. 32 is a circuit diagram showing another example of a constant heating control circuit.

FIG. 32 shows another example of a constant temperature control circuit. An electric current detecting device 42 detects an electric current flowing through the heater 33. A quotient operation unit 43 detects a quotient V/I by dividing a heater voltage V by a detection electric current I. The quotient is proportional to the resistance of the heater 33. A voltage proportional to the reference resistance is set by the potentiometer (variable resistor) 30 and a constant voltage source 44 and is compared by the defferencial amplifier 37 with the output voltage from the quotient operation unit 43. According to a differential output, the power control transistor 36 is controlled to make the sensor temperature constant.

Power may be continuously supplied to the heater whose temperature is to be kept constant. However, in order to decrease power loss and hence a rise in temperature, power may be intermittently supplied to the heater in accordance with a switching control method. In this case, the period is preferably 1 [ms] to 100 [ms] in consideration of temperature stability.

Figure 33:
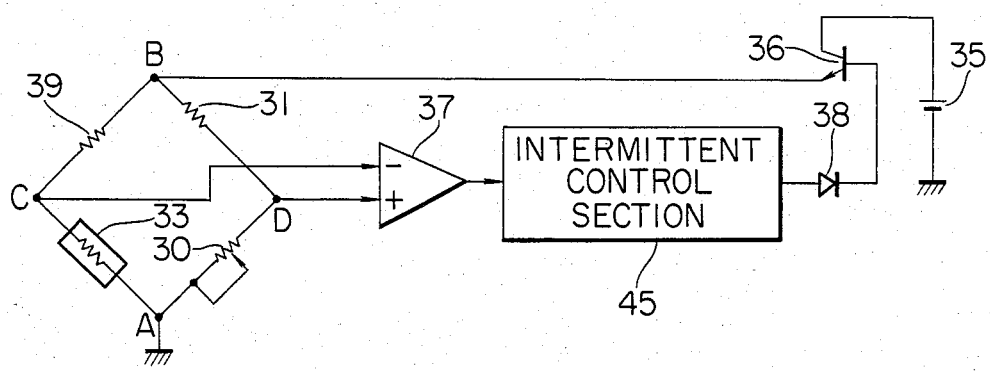
FIG. 33 is a circuit diagram of a constant temperature control circuit with an intermittent control section.

FIG. 33 shows still another example of a constant temperature control circuit for controlling power in accordance with the switching method. An intermittent control section 45 is arranged between the differential amplifier (measuring amplifier) 37 and the power control transistor 36.

Figure 34:
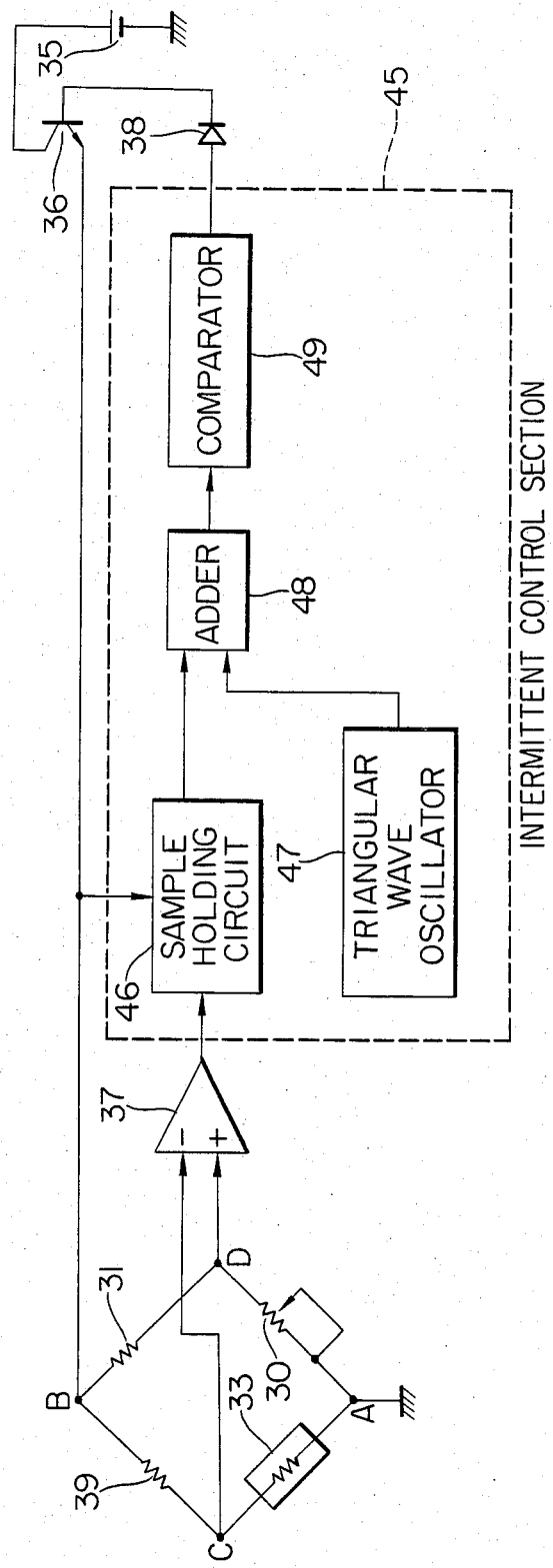
FIG. 34 is a detailed block diagram of the intermittent control section shown in FIG. 33.

FIG. 34 is a detailed block diagram of the intermittent control section 45 shown in FIG. 33. In the switching method, an unbalanced voltage is obtained when the intermittent control section 45 is ON. However, when the section 45 is OFF, no unbalanced voltage is obtained. Therefore, the unbalanced voltage in the ON period is held in a sample holding circuit 46. Meanwhile, a triangular wave oscillator 47 oscillates a triangular or similar voltage wave. An output from the sample holding circuit 46 and an output (voltage) from the triangular wave oscillator 47 are added by an adder 48. An output from the adder 48 is supplied to a comparator 49 and is shaped to be a rectangular wave with ON and OFF states. While the heater temperature is low, the ratio of ON time to OFF time is set to be high. However, when the heater temperature is high, the ratio of ON time to OFF time is set to be low. Thus, the sensor temperature can be kept constant. When the power control transistor is ON or OFF, only a small power loss occurs. Only in the switching or transient state from ON time to OFF time and vice versa, does a relatively large power loss occurs. As a result, average power loss is small and the resulting temperature rise due to the slight power loss is also small. The switching method described above is an excellent and very practical method when the heater is used on an automobile and located near a high temperature of 130 [°C.], that is, when a high reliability is required and reliability of a transistor is degraded at a high temperature. The switching method may not be limited to ON time and OFF time. A two-state switching method for selectively switching high power and low power may also be utilized. According to this method, the unbalanced voltage is continuously applied, resulting in convenience.

Figure 35:
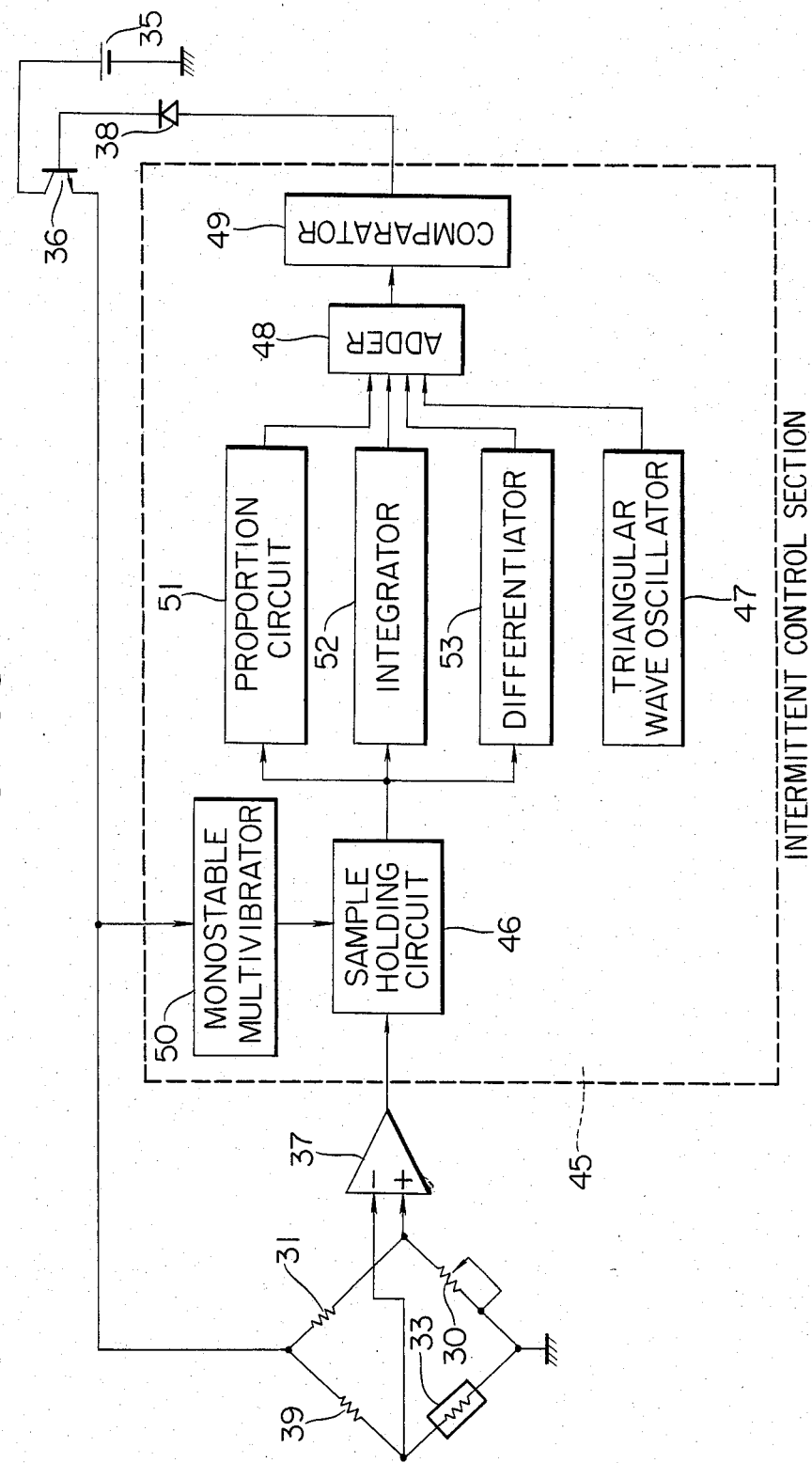
FIG. 35 is a detailed block diagram showing another intermittent control section.

FIG. 35 is another example of the intermittent control section 45. An output from the sample holding circuit 46 is supplied to a proportion circuit 51, an integrator 52 and a differentiator 53. Outputs from the proportion circuit 51, the integrator 52, the differentiator 53 and the triangular wave oscillator 47 are added by the adder 48 to perform stable control.

The intermittent control sections 45 shown in FIGS. 34 and 35 may be used in the constant temperature control circuit shown in FIG. 32 in the same manner.

In summary, the present invention provides the following advantages:

(1) Since the heater is deposited on the limiting electric current type oxygen sensor through the insulating film, excellent heat conduction is performed between the oxygen concentration detection section and the heater. Only power of 0.5 [W] to 3.5 [W] is required to heat the sensor to a temperature of 700 [°C.] at an air velocity of 0 to 50 [m/s]. The power required in the heater of the present invention is about 1/15 to 1/25 that of the conventional sheath heater for heating the oxygen sensor from its side surface.

(2) Since the thin film thickness, the porosity, the average pore diameter, and the size of a hole formed in the insulating film, which are important factors to regulate the flow rate of oxygen gas, are quantitatively determined, uniform characteristics can be obtained with good reproducibility.

(3) Since Rh is added to Pt to form an alloy as a material as the heater, the heater is stably operated and provides long service life.

(4) Since the resistance of the heater is detected to control the temperature, a separate heat-sensitive element is not required. Furthermore, the temperature detection delay may not occur.

As may be apparent from the various characteristics described above, the limiting electric current type oxygen sensor according to the present invention can be effectively used as an automobile oxygen sensor in the "lean" mixture.

What is claimed is:

1. A limiting electric current type oxygen concentration detecting device, comprising:
a limiting electric current type oxygen sensor with a microheater including an oxygen ionic conductor, an anode and a cathode respectively formed on two major surfaces of said oxygen ionic conductor, an insulating film which has a porosity between 0.2 and 3.1%, an average pore diameter between 140 Å and 190 Å, and a thickness between 0.6 and 10 μm, and which is formed on one of said anode and said cathode to regulate the flow rate of oxygen gas to provide electrical insulation, said microheater being on said insulating film, whereby said oxygen ionic conductor is electrically insulated from said heater through said insulating film; and
constant temperature control circuit means for detecting the temperature of said microheater by measuring the resistance thereof so as to keep the heater temperature constant in accordance with the detection of the temperature.

2. A detecting device according to claim 1, further comprising a hole which regulates the flow rate of the oxygen gas, said hole having an area which is not less than 1/33 of an area of said one of said anode and cathode.

3. A detecting device according to claim 1, wherein said constant temperature control circuit means comprises: a Wheatstone bridge having said microheater at one side thereof; an amplifier for amplifying an unbalanced voltage appearing at one of two pairs of opposing terminals of said Wheatstone bridge; and a control circuit for supplying power to the other one of said two pairs of opposing terminals of said Wheatstone bridge on the basis of the output from said amplifier.

4. A detecting device according to claim 3, wherein said control circuit means further comprises:

an intermittent control circuit having a sample holding circuit for holding the output from said amplifier so as to control power supply to said Wheatstone bridge by starting and stopping the power supply in response to the output from said amplifier, a triangular wave oscillator, an adder for adding an output from said sample holding circuit and an output from said triangular wave oscillator, and a comparator for comparing an output from said adder and a reference value to produce an ON/OFF signal; and a power transistor which is switched by an output from said intermittent control circuit.

5. A detecting device according to claim 3, wherein said constant temperature control circuit means further comprises: a power source for supplying power to said microheater; electric current detecting means for detecting electric current flowing from said power source to said microheater; operating means for computing electrical resistance of said microheater from the electric current detected by said electric current detecting means and from the voltage applied by said power source; an operational amplifier for amplifying the difference between an output voltage which represents the electrical resistance of said microheater and is produced by said operating means and the output from said operational amplifier; and a power transistor for controlling power supplied from said power source to said microheater on the basis of the output from said operational amplifier.

6. A detecting device according to claim 1, wherein said microheater comprises a member selected from the group consisting of platinum and alloys thereof containing up to 60% by weight of rhodium.

7. A detecting device according to claim 1 wherein said microheater is integrally formed on said insulating film so as to be in direct contact therewith.

8. A detecting device according to claim 7 wherein the microheater is exposed to the gas whose flow rate is regulated by the insulating film.

* * * * *